US012031964B2

(12) United States Patent
Wambugu et al.

(10) Patent No.: US 12,031,964 B2
(45) Date of Patent: Jul. 9, 2024

(54) ENHANCING SPATIAL AND TEMPORAL RESOLUTION OF GREENHOUSE GAS EMISSION ESTIMATES FOR AGRICULTURAL FIELDS USING COHORT ANALYSIS TECHNIQUES

(71) Applicant: International Business Machines Corporation, Armonk, NY (US)

(72) Inventors: Isaac Waweru Wambugu, Nairobi (KE); Ranjini Bangalore Guruprasad, Bangalore (IN); Manikandan Padmanaban, Bangalore (IN); Kumar Saurav, Bangalore (IN); Ivan Kayongo, Nairobi (KE); Jagabondhu Hazra, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 388 days.

(21) Appl. No.: 17/495,582

(22) Filed: Oct. 6, 2021

(65) Prior Publication Data

US 2023/0106473 A1    Apr. 6, 2023

(51) Int. Cl.
G01N 33/00    (2006.01)
(52) U.S. Cl.
CPC ............................. G01N 33/0036 (2013.01)
(58) Field of Classification Search
CPC .............................................. G01N 33/0036
(Continued)

(56) References Cited

U.S. PATENT DOCUMENTS 7,966,971 B2    6/2011  Zimmerman
8,595,020 B2    11/2013 Marino
(Continued)

FOREIGN PATENT DOCUMENTS

AU    2016203849 B2    6/2016
CN      103714507 A    4/2014
(Continued)

OTHER PUBLICATIONS

Hamrani, et al. Machine Learning for Predicting Greenhouse Gas Emissions from Agricultural Soils, 741 Science of the Total Environment 140338 (2020).
(Continued)

*Primary Examiner* — John H Le
(74) *Attorney, Agent, or Firm* — Ryan, Mason & Lewis, LLP (57) ABSTRACT

Methods, systems, and computer program products for enhancing spatial and temporal resolution of greenhouse gas emission estimates for agricultural fields using cohort analysis techniques are provided herein. A computer-implemented method includes obtaining non-greenhouse gas remote sensing data and contextual information pertaining to agricultural fields; determining cohorts among the agricultural fields by deriving agricultural field-specific features from the obtained data and contextual information; computing agricultural field-level time series of greenhouse gas emission estimates for the cohorts by processing the obtained data and contextual information using a process-based model; calculating bias corrections for the cohorts by processing, using a time series learning model, the time series and background greenhouse gas emission estimates; generating resolution-enhanced greenhouse gas emission estimates for the cohorts based on initial greenhouse gas emission estimates derived from greenhouse gas remote sensing data and the calculated (Continued)

bias corrections; and performing automated actions based on the updated greenhouse gas emission estimates.

20 Claims, 8 Drawing Sheets

(58) Field of Classification Search
USPC .......................................................... 702/2
See application file for complete search history.

(56) References Cited

U.S. PATENT DOCUMENTS

| | | | |
|---|---|---|---|
| 11,704,581 | B1 | 7/2023 | McEntire et al. |
| 2009/0288606 | A1 | 11/2009 | Zimmerman |
| 2011/0313666 | A1 | 12/2011 | Hirvo |
| 2013/0080213 | A1* | 3/2013 | Peters ............... G06Q 10/10 705/7.38 |
| 2013/0179078 | A1 | 7/2013 | Griffon |
| 2014/0172323 | A1 | 6/2014 | Marino |
| 2018/0156766 | A1 | 6/2018 | Zeng et al. |
| 2019/0333163 | A1 | 10/2019 | Perry et al. |
| 2020/0027096 | A1 | 1/2020 | Cooner |
| 2020/0256978 | A1 | 8/2020 | Klein |
| 2020/0275617 | A1 | 9/2020 | Fabijanski et al. |
| 2021/0010993 | A1 | 1/2021 | Shibata |
| 2021/0199600 | A1 | 7/2021 | Das et al. |
| 2021/0224927 | A1 | 7/2021 | Perry |
| 2022/0117215 | A1 | 4/2022 | Sibley |
| 2022/0139081 | A1 | 5/2022 | Mohite |
| 2022/0412553 | A1 | 12/2022 | Haddad |

FOREIGN PATENT DOCUMENTS

| | | |
|---|---|---|
| CN | 104657566 A | 5/2015 |
| CN | 111178789 A | 5/2020 |
| CN | 111896680 A | 11/2020 |
| KR | 20110017816 | 2/2011 |
| WO | 2017048002 A1 | 3/2017 |

OTHER PUBLICATIONS

Shi et al., PeerJ, Herbicide applications increase greenhouse gas emissions of alfalfa pasture in the inland arid region of northwest China, May 25, 2020.

Min et al., DeNitrification-DeComposition (DNDC) Improvement through Model Coupling and Sub-model Development Considering Agricultural Land Use and Future Climate Change, Journal of Environmental Biology • Mar. 2017.

Babu et al., Field Validation of DNDC Model for Methane and Nitrous Oxide Emissions from Rice-based Production Systems of India, Nutrient Cycling in Agroecosystems vol. 74, pp. 157-174 (2006).

Cai et al., Global Biochemical Cycles, Field validation of the DNDC model for greenhouse gas emissions in East Asian cropping systems, Nov. 2003.

Unglesbee, E., DTN.com, Temperature Inversions Increase Risk of Herbicide Drift, Feb. 2017.

Jiang et al., Atmospheric Environment, Application of herbicides is likely to reduce greenhouse gas (N2O and CH4) emissions from rice-wheat cropping systems, vol. 107, Apr. 2015, pp. 62-69.

Kachar et al., Int. Arch. Photogramm. Remote Sens. Spatial Inf. Sci., Detection and Modeling of Temperature Inversion in the Atmosphere Using Modis Images (Case Study: Kermanshah), Dec. 2015.

IBM.com, The Weather company sample, https://www.ibm.com/docs/en/cognos-analytics/11.1.0?topic=s-weather-company-sample, 2021.

Wu et al., Insects, An Advanced Numerical Trajectory Model Tracks a Corn Earworm Moth Migration Event in Texas, USA, Sep. 2018.

Tonnang et al., Ecological Modelling, Advances in crop insect modelling methods—Towards a whole system approach, Jun. 2017.

Gevirtz et al., 1995. Environmental Management Framework Databases Developed Utilizing High-Resolution Satellite Imagery and Their Utility for Environmental Monitoring: Abstract. AAPG Bulletin, 79.

Li et al., (2005) High-Resolution Satellite Image Sources for Disaster Management in Urban Areas. Geo-information for Disaster Management. Springer, Berlin, Heidelberg.

Ranchin, T. Multisensor Fusion, Data Fusion in Remote Sensing and Improvement of the Spatial Resolution of Satellite Images, 2002.

Guo et al., Assessment of Global Carbon Dioxide Concentration Using MODIS and GOSAT Data. Sensors 2012, 12, 16368-16389.

Cui et al., A Soil Moisture Spatial and Temporal Resolution Improving Algorithm Based on Multi-Source Remote Sensing Data and GRNN Model, Feb. 2020.

Nassar et al., (2013). Improving the temporal and spatial distribution of co2 emissions from global fossil fuel emission data sets. Journal of Geophysical Research Atmospheres, 118(2), 917-933.

Fong et al., World Resources Institute, Global Protocol for Community-Scale Greenhouse Gas Emission Inventories, 2014.

List of IBM Patents or Patent Applications Treated as Related.

Thompson et al., Crop Protection, Potential for automatic weed detection and selective herbicide application, vol. 10, Issue 4, Aug. 1991, pp. 254-259.

Wang et al., Computers and Electronics in Agriculture, A review on weed detection using ground-based machine vision and image processing techniques, vol. 158, Mar. 2019, pp. 226-240.

Cui et al., Improving the DNDC biogeochemistry model to simulate soil temperature and emissions of nitrous oxide and carbon dioxide in cold regions, Science of The Total Environment, vol. 687, 2019.

Abdurrahman, Stubble Burning Effects on Health & Environment, Regulation, and Management Practices, Dec. 2020, Science Direct, vol. 2, pp. 1-27 (Year 2020).

* cited by examiner

ENHANCING SPATIAL AND TEMPORAL RESOLUTION OF GREENHOUSE GAS EMISSION ESTIMATES FOR AGRICULTURAL FIELDS USING COHORT ANALYSIS TECHNIQUES

BACKGROUND

The present application generally relates to information technology and, more particularly, to climate-related technologies. More specifically, scientists have identified several greenhouse gases (GHG) that are at least partially responsible for the increase in global temperatures, including, for example, carbon dioxide (CO2), nitrogen oxide (N2O), methane (CH4), fluorinated gases, etc. Reducing emissions of such GHG typically involves GHG measurements. However, implementing sensors to measure the emission of such gases is not plausible for agricultural sectors wherein GHG emissions commonly occur in open fields from fertilizers, energy from irrigation, mechanization from planting and harvesting, etc. Additionally, while remote sensed data from satellites can provide global GHG emission data, attributing portions of such emissions to agricultural sectors is challenging, and data from such satellites face accuracy problems due, for example, to cloud cover, as well as low spatial resolution and wide temporal resolution.

SUMMARY

In one embodiment of the present invention, techniques for enhancing spatial and temporal resolution of GHG emission estimates for agricultural fields using cohort analysis techniques are provided. An exemplary computer-implemented method can include obtaining non-greenhouse gas remote sensing data pertaining to at least a portion of multiple agricultural fields, and contextual information pertaining to at least a portion of the multiple agricultural fields. The method also includes determining one or more cohorts among the multiple agricultural fields based at least in part on deriving one or more agricultural field-specific features from at least a portion of the obtained non-greenhouse gas remote sensing data and at least a portion of the obtained contextual information, and computing at least one agricultural field-level time series of greenhouse gas emission estimates for each of the one or more cohorts by processing at least a portion of the obtained non-greenhouse gas remote sensing data and at least a portion of the obtained contextual information using at least one process-based model. Additionally, the method includes calculating at least one bias correction for each of the one or more cohorts by processing, using a time series learning model, the at least one agricultural field-level time series of greenhouse gas emission estimates and one or more background greenhouse gas emission estimates pertaining to at least a portion of the one or more cohorts. Further, the method includes generating at least one updated greenhouse gas emission estimate for at least a portion of the one or more cohorts based at least in part on at least one initial greenhouse gas emission estimate derived from greenhouse gas remote sensing data pertaining to at least a portion of the multiple agricultural fields and the at least one calculated bias correction for the at least a portion of the one or more cohorts, wherein the at least one updated greenhouse gas emission estimate includes enhanced spatial resolution and temporal resolution as compared to the at least one initial greenhouse gas emission estimate. Also, the method additionally includes performing one or more automated actions based at least in part on the at least one updated greenhouse gas emission estimate.

Another embodiment of the invention or elements thereof can be implemented in the form of a computer program product tangibly embodying computer readable instructions which, when implemented, cause a computer to carry out a plurality of method steps, as described herein. Furthermore, another embodiment of the invention or elements thereof can be implemented in the form of a system including a memory and at least one processor that is coupled to the memory and configured to perform noted method steps. Yet further, another embodiment of the invention or elements thereof can be implemented in the form of means for carrying out the method steps described herein, or elements thereof; the means can include hardware module(s) or a combination of hardware and software modules, wherein the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

As described herein, at least one embodiment of the invention includes enhancing spatial and temporal resolution of GHG emission estimates for agricultural fields using cohort analysis techniques. Such an embodiment includes leveraging the value of non-GHG remote sensing data to enhance the spatial resolution of GHG emission estimates for agricultural fields, and leveraging contextual information to enhance the temporal resolution of GHG emission estimates for agricultural fields.

As further detailed herein, one or more embodiments include identifying cohorts of agricultural fields based at least in part on non-GHG remote sensing data. Additionally, for each of the identified cohorts, GHG emissions are estimated using one or more process-based models. As used herein, process-based models attempt to simulate underlying biogeochemical processes and can be responsive, for example, to the effects of soil properties, climate, and management. Examples of process-based models that can be used for GHG estimation purposes include a DeNitrification-DeComposition (DNDC) model, a DayCent model, and a Rothamsted carbon (RothC) model.

Further, at least one embodiment includes leveraging one or more time series learning models to estimate actual GHG estimates at a given temporal resolution (e.g., a daily temporal resolution) using one or more background emission sources derived from contextual information (e.g., daily resolution data) along with process-based model GHG estimates (e.g., daily estimates) of the given cohort. By way of example, such time series data can be processed using at least one linear regression model, at least one multilayer perceptron model, and/or at least one sequential minimal optimization regressor model found in support vector machines (SVM). Such example models can be used for GHG emission estimates, quantification and prediction. Accordingly, such embodiments can include determining GHG emissions for a given agricultural field at the spatial resolution of non-GHG remote sensing data (i.e., enhanced and/or improved resolution from conventional GHG satellite data) and enhanced temporal resolution (e.g., daily temporal resolution).

One or more embodiments thereby include intelligently facilitating accurate gap-filling in GHG satellite data based at least in part on analysis of static and dynamic GHG-related data. Such an embodiment can include, for example, analyzing the current context of at least one specific geographic location and identifying a cohort of one or more agricultural fields. Additionally, such an embodiment also includes analyzing physical factor data such as weather-related data, seasonal data, vegetative cover data, etc., as well as economic factor data and calendar data such as agricultural show information, carnival information, etc. Such an embodiment can further include using one or more static models to analyze the GHG emissions from the cohort, wherein the results of the model are then provided to and/or processed by a DNDC model, which generates at least one output used for gap-filling GHG satellite data in one or more relevant agricultural regions.

As noted above and further used herein, static models refer to models with inherent methods and/or functions and data which are less likely to change in the spatial dimension and/or the temporal dimension. Accordingly, such models typically do not require forecasting or predicting when computing GHG emissions. Additionally, in one or more embodiments, static models use contextual information such as, for example, weather data, calendar events data, regional data, etc., as inputs to help optimize input data from one or more satellites and/or from a relevant cohort.

The DNDC model, on the other hand, is a process-based model that simulates details of physical and biological processes (e.g., processes in the soil). In at least one embodiment, such a model takes inputs of fertilizer levels, tillage system data, climate scenarios, soil temperature data, soil moisture level data, etc., and such inputs can be optimized through contextual data that originate from the static model(s). In such an embodiment, process-based models (e.g., such as a DNDC model) do not capture other aspects relating to GHG estimation such as soil disturbance, change in biomass, change in farming practices, etc., which can be captured through contextual data; thus the need for and/or use of static models results as an input to the DNDC model. Accordingly, a DNDC model simulates the process responsible for GHG emission from an agroecosystem, and bridges the chemical reactions in soil with the ecological drivers (e.g., climate, soil, vegetation, farming practices, etc.) and environmental factors (e.g., temperature, moisture, pH and Eh, etc.), and simulates carbon and nitrogen dynamics.

Additionally, at least one embodiment includes using in-distribution (ID) and out-of-distribution (OOD) techniques using auxiliary information, such as additional input features from contextual data, to improve GHG estimation. Such an embodiment includes extrapolating at least one OOD feature space across geographic terrain to create a globally applicable model. Using satellite imagery and events calendar data, one or more embodiments include segregating the emission factors in a specific locale. For example, when calculating the GHG emission in a day for a certain farming location, it can be assumed that nitrous oxide is the main pollutant. Therefore, in the case of a transactional showcase and/or festival week, which may result in increased GHG emission, the extra emission factor can be classified as $CO_2$ from increased transport activities. The same can be validated, for example, from satellite imagery of the area.

Advantages of one or more embodiments, as detailed herein, can include, for example, enhanced measurement of GHG emissions, creating a global dataset for emission analysis, and providing a scalable solution for GHG emission estimations.

As detailed herein, non-GHG satellites often have lower spatial and temporal resolution (e.g., with some satellites passing daily and others having a spatial resolution of, for instance, one kilometer by one kilometer). One or more embodiments includes retrieving such imagery data from one or more satellites and using computer vision to extract one or more features (from at least a portion of the imagery data). For instance, such an embodiment can include approximating the number of vehicles in motion in a certain locality, the types of crops grown in the locality, economic activity in the locality, agricultural activities in the locality, farming practices in the locality, weather information for the locality, climatic seasons for the locality, etc. Using a knowledge base that tracks emissions from such activities, at least one embodiment includes estimating GHG emissions at a certain cohort, as further described herein.

Additionally, such an embodiment can include utilizing machine learning techniques to conduct gap-filling and scale the data from a cohort to specific geographical areas with identical agricultural features.

As further detailed herein and below, one or more embodiments include using non-GHG satellite data to estimate context-based non-GHG satellite data, which can serve as indicators, for example, of farming practices. By way merely of example, such an embodiment can include identifying the growth stages of different crops by observing and/or processing the normalized difference vegetation index (NDVI) and the normalized difference water index (NDWI) (e.g., from MODIS). Additionally or alternatively, based on biomass data, leaf area index and/or percentage of vegetative cover, such an embodiment can include identifying planting and harvesting seasons. Using a related knowledge base, such an embodiment can also include identify emissions from different crop types at different growing stages.

At least one embodiment can also include using satellite data to determine and/or identify landmass size containing and/or pertaining to a specific crop type. Such size or area information can be used, for example, to determine and/or estimate expected emissions in a certain cohort. Such satellite data typically have better temporal resolution (than other GHG-related data) that can be used to identify one or more signals that may cause an anomaly in the data (such as, for example, stubble burning).

Additionally, one or more embodiments include using calendar data to estimate GHG emissions. Calendar data (e.g., data pertaining to events) provide important and/or salient periods of time that are associated with increased activity that may inflate emissions for certain periods and/or localities. Such data can be useful, for example, for segregating one or more emission factors and/or identifying the source(s) of GHG emissions.

Also, at least one embodiment includes using weather data, climate data, and micro-climate events data to estimate GHG emissions. Such data can play a significant role in correcting GHG data (e.g., when conducting segregation techniques). For example, weather data (such as, e.g., precipitation data and soil moisture data) may help identify irrigation data and information pertaining to the frequency of irrigation. Using such information, an example embodiment can include identifying if irrigation was conducted on a given farm and, based on the size of the farm, identifying the amount of energy needed to irrigate one or more farms in a specific and/or related cohort.

Accordingly, at least one embodiment includes enhancing spatial and temporal resolution of GHG emission estimates for farms and/or other agricultural fields using GHG and non-GHG satellite data. Such an embodiment includes collecting non-GHG remote sensing data (e.g., optical data, microwave data, etc.) from satellites and/or other sources, contextual information (e.g., calendar events, traffic information, residential power consumption, etc.) from crowd-sourcing and/or third-party systems, night light remote sensing data, regional farming practices data, location data for background emissions from existing knowledge bases, weather data, and local soil conditions data, etc. Additionally, such an embodiment includes identifying one or more cohorts (e.g., members separated geographically) of farms and/or other agricultural fields based on one or more farm-specific features (e.g., vegetation type, farming practices, crop cycles, crop acreage, etc.) derived by processing at least a portion of the above-noted non-GHG remote sensing data.

Such an embodiment also includes generating at least one knowledge base of time series GHG estimate data at the spatial resolution of non-GHG remote sensing data (i.e., finer in resolution than conventional GHG satellite data) and at a given temporal resolution (e.g., daily temporal resolution) for each of the identified cohorts using a combination of weather information and process-based models. Further, such an embodiment can include estimating a cohort similarity score for any new farm region of interest, at the spatial resolution of non-GHG remote sensing data, and computing the time series of GHG emission estimates based on the given temporal resolution (e.g., daily temporal resolution). As further detailed herein, such an embodiment additionally includes estimating GHG emissions at the spatial resolution of non-GHG remote sensing data and at the given (e.g., daily) temporal resolution by learning at least one bias correction for GHG emission estimates based on the GHG remote sensing data, cohort-based GHG emission estimates, and one or more derived background emissions.

Figure 1:
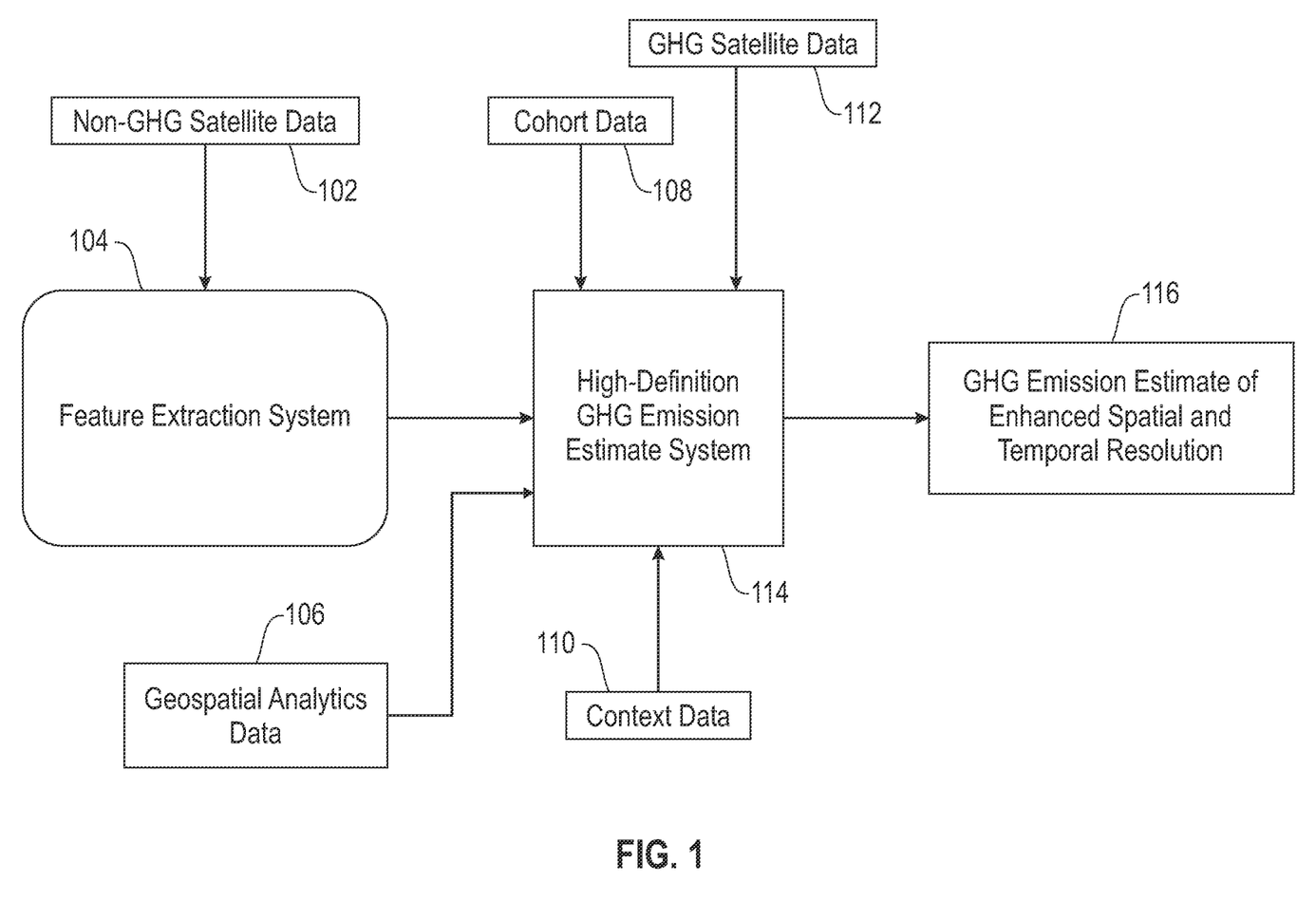
FIG. 1 is a diagram illustrating system architecture, according to an exemplary embodiment of the invention.

FIG. 1 is a diagram illustrating system architecture, according to an embodiment of the invention. By way of illustration, FIG. 1 depicts non-GHG satellite data 102, which is processed by feature extraction system 104 (which can include, for example, computer vision, boundary detection, synthetic-aperture radar (SAR) reflectance, crop identification techniques, etc.) to extract (from at least a portion of the non-GHG satellite data 102) one or more features and provide the features to high-definition GHG emission estimate system 114. Also provided as input to high-definition GHG emission estimate system 114 are geospatial analytics data 106, cohort data 108, context data 110 (e.g., calendar data, events data, etc.), and GHG satellite data 112. Based at least in part on processing such inputs, the high-definition GHG emission estimate system 114 generates at least one GHG emission estimate 116 of enhanced spatial and temporal resolution (as compared to conventional estimates and/or process-based model estimates).

By way merely of example, an embodiment such as depicted in FIG. 1 can include processing cohort data 108 using a process-based model and/or a physical-based model (e.g., a DNDC model), as part of high-definition GHG emission estimate system 114, to determine an initial GHG emission estimate for a given farm. Subsequently, such an example embodiment includes using context data 110 (e.g., calendar events data) to determine contextual information such as planning and harvesting seasons of a cohort, farming activities for the cohort (e.g., fertilizer application seasons, etc.), etc. Using such estimates and determinations, in addition to further input data (such as noted above and depicted in FIG. 1, high-definition GHG emission estimate system 114 corrects and/or updates missing data from GHG satellite data 112, and generates a GHG emission estimate of enhanced spatial and temporal resolution 116 for the given farm.

Figure 2:
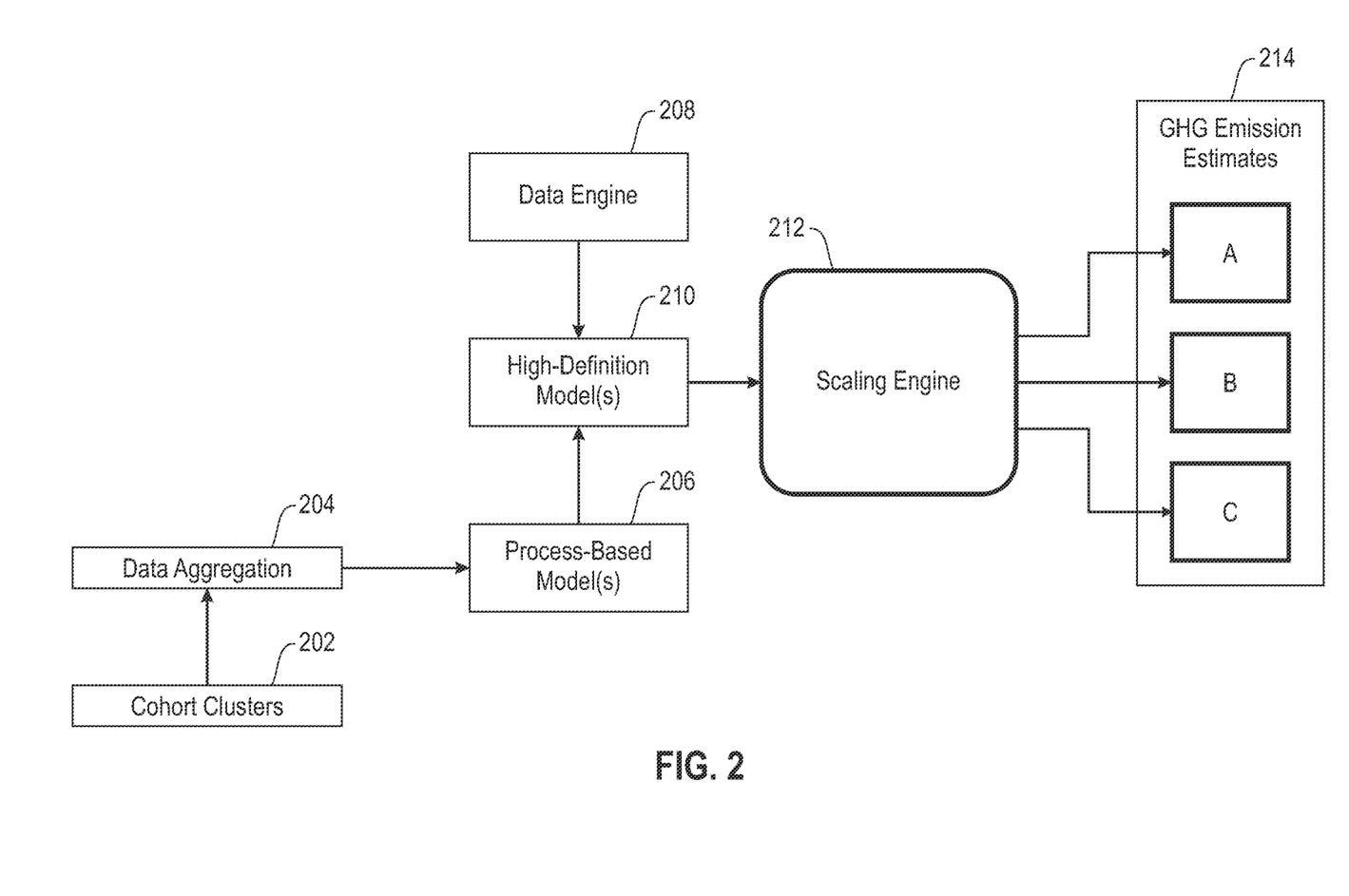
FIG. 2 is a diagram illustrating system architecture, according to an exemplary embodiment of the invention.

FIG. 2 is a diagram illustrating system architecture, according to an exemplary embodiment of the invention. By way of illustration, FIG. 2 depicts data pertaining to one or more cohort clusters 202, which is processed by data aggregation component 204, and ultimately processed by one or more process-based models 206 (e.g., DNDC models). The output (e.g., an initial GHG emission estimate for a given cohort or farm) generated by process-based model(s) 206 is provided as input to one or more high-definition models 210, along with input from data engine 208 (which processes satellite data, geospatial data, environmental data, etc.). The high-definition model(s) 210 generate an updated GHG emission estimate (updated with enhanced spatial and temporal resolution) and provide the updated estimate to scaling engine 212, which scales the updated estimate to generate multiple GHG emission estimates 214 for multiple similar farms and/or cohort members (e.g., members A, B, and C).

With respect to scaling an updated estimate, most data estimates do not align to geographical boundaries. To meet such inventory boundaries, at least one embodiment includes adjusting for changes using location-based scaling factors. Such scaling factors can include the ratio between available data and the required inventory data. For instance, when conducting a GHG estimate in connection with an agricultural region that is proximate to an urban center, contextual information such as population and city-specific data will be a factor in developing the scaling factor(s). Thereby, in one or more embodiments, inventory data can be quantified as follows: (scaling factor data point for inventory/scaling factor data point for original data)*(available emissions data). Moreover, different gases have different scaling factors. For example, if the GHG gas under study is carbon dioxide, the scaling factor used will be different from that of methane or nitrous oxide.

Figure 3:
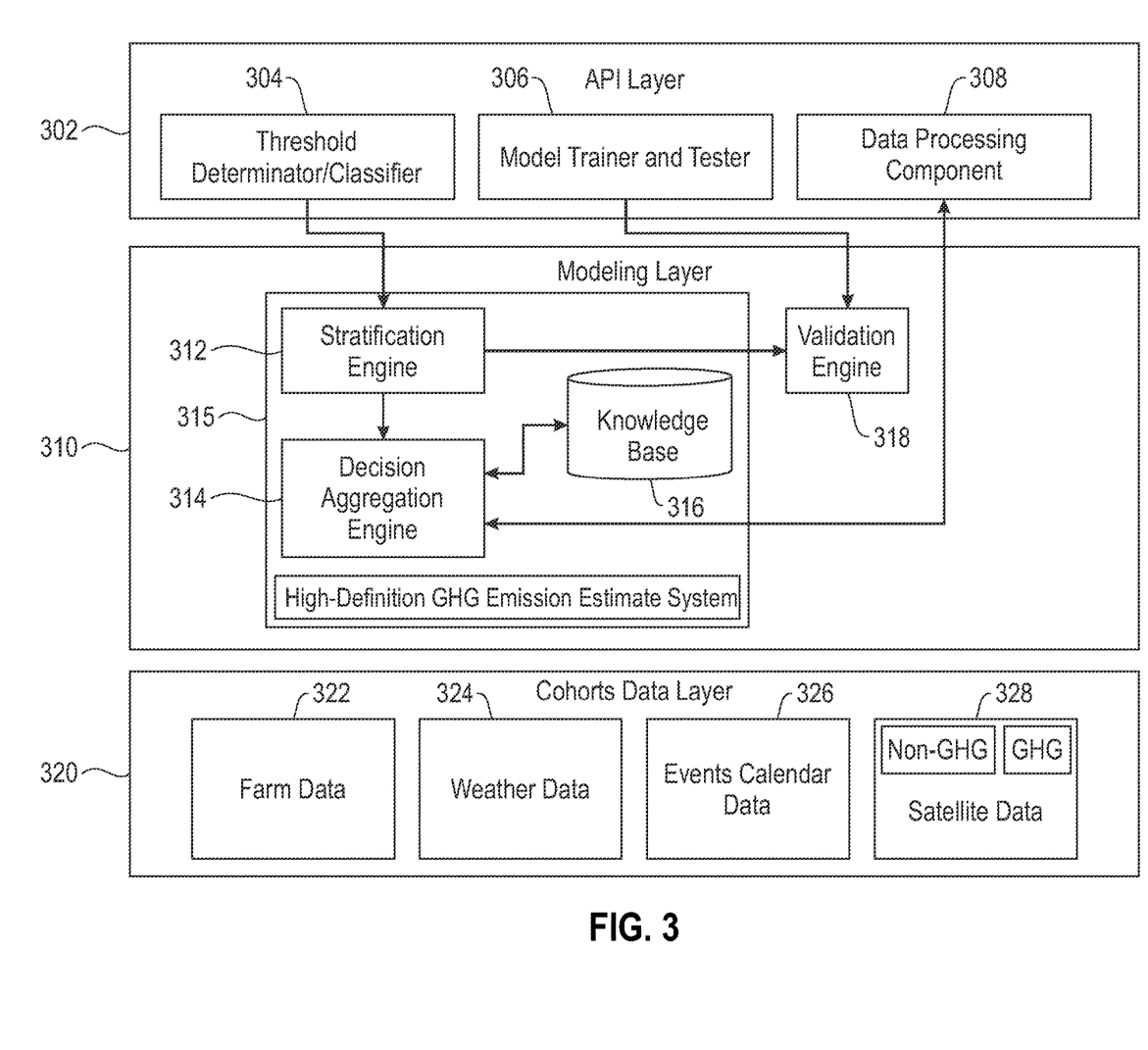
FIG. 3 is a diagram illustrating system architecture, according to an exemplary embodiment of the invention.

FIG. 3 is a diagram illustrating system architecture, according to an exemplary embodiment of the invention. By way of illustration, FIG. 3 depicts an application programming interface (API) layer 302, which includes a threshold determinator/classifier 304, a model trainer and tester 306, and a data preprocessing component 308. FIG. 3 also depicts a modeling layer 310, which includes a validation engine 318 as well as a high-definition GHG emission estimate system 315, which includes a stratification engine 312, a decision aggregation engine 314, and a knowledge base 316. Further, as also depicted, FIG. 3 includes a cohorts data layer 320, which includes farm data 322, weather data 324, events calendar data 326, and satellite data 328 (which can include non-GHG data and GHG data).

In at least one embodiment, the cohorts data layer 320 is the initial stage that provides the input data used by the high-definition GHG emission estimate system 315. Such data, as noted above, can include farm data 322 from the cohort as well as inventory data for the region, weather data 324, contextual data such as calendar events data 326, and satellite data 328 including both GHG and non-GHG satellite data.

In one or more embodiments, such data flows to the decision aggregation engine 314, which contains decision rules for aggregation and provides the logic of how the cohort data integrates with the satellite data. Additionally or alternatively, the data from the cohorts data layer 320 may require preprocessing before being used by high-definition GHG emission estimate system 315. The data preprocessing component 308 is used for this purpose, and ensures the data are in a format that can be understood by the other components as well as in connection with other functions such as outlier detection and elimination, gap filling, feature reduction, etc. Once the data are preprocessed, the data are returned to the decision aggregation engine 314.

The decision aggregation engine 314 makes a decision on the scaling factor to be used during the integration process. For example, the data from one or more satellites and from one or more farms can be of different temporal and spatial resolution. The decision aggregation engine 314 determines the scaling factor to use to alter the satellite data in order to retrieve a spatial and temporal resolution similar to (e.g., the same as) that of the farm data, and/or vice versa if need be. Such scaling factors are computed using knowledge base 316, which stores contextual data, historical data and/or mathematical methods and formulae that can be retrieved by the decision aggregation engine 314.

Also, the emission data are segregated into individual components using the stratification engine 312, which uses one or more thresholds set by the threshold determinator/classifier 304. The segregated emission estimates are then sent to the validation engine 318, which checks to determine if the estimate meets the one or more expected thresholds. In one or more embodiments, the validation engine 318 is configured by the model trainer and tester, 306 which performs cross-validation on the estimates to ensure validity.

Figure 4:
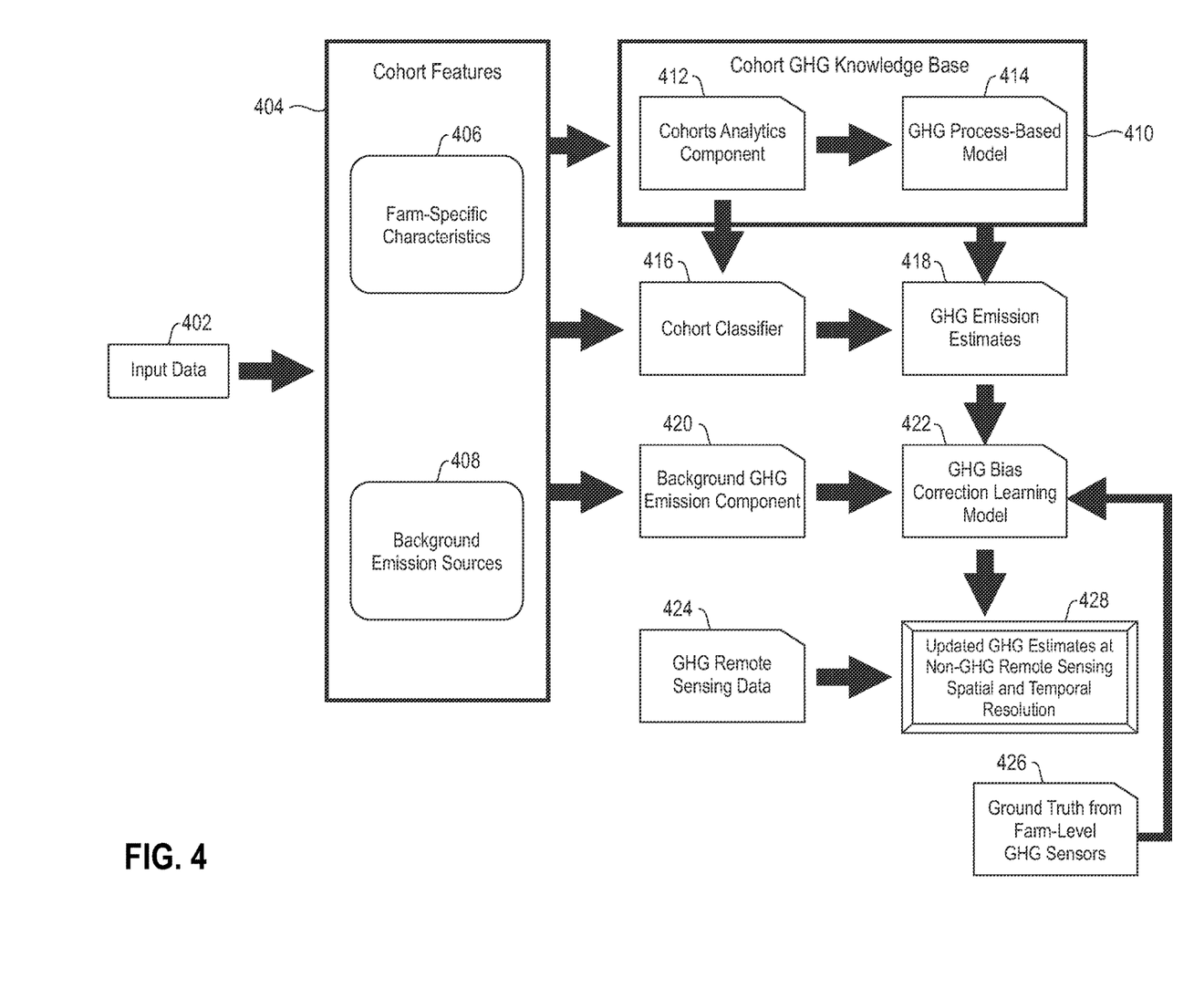
FIG. 4 is a diagram illustrating system methodology, according to an exemplary embodiment of the invention.

FIG. 4 is a diagram illustrating system methodology, according to an exemplary embodiment of the invention. By way of illustration, FIG. 4 depicts steps of cohort identification and related GHG emission estimate knowledge base creation and/or implementation. Specifically, input data 402, which can include, for example, non-GHG remote sensing data (e.g., optical data, microwave data, etc.), weather data, calendar events data, night light remote sensing data, traffic data, geolocation data, regional farming practices data, and background GHG emission source data, are processed to determine cohort features 404, which can include farm-specific characteristics 406 (e.g., crop types, irrigation information, manure information, pesticide types and application schedules, soil types and moisture levels, etc.) and background GHG emission sources 408 (e.g., information pertaining to bodies of water (such as size, sub-surface temperature), information pertaining to power plants (such as capacity and production profile), information pertaining to relevant residential areas (such as density), transportation data, forest fire information, etc.).

By way of example, for non-GHG satellite data, at least one embodiment includes identifying usable and unusable data (from input data 402) due to satellite limitations such as cloud cover (e.g., using at least one cloud flag), etc. Such an identification process can serve as a basis of identifying one or more cohorts. In one or more example embodiments, usable satellite data regions are denoted as "green points," while unusable satellite data regions are denoted as "red points," and the green points are used for identifying the cohort(s).

One or more such embodiments also include identifying additional contextual features that can act as a feature space for identifying one or more cohorts. The additional features can be estimated using non-GHG satellite data and/or crowdsourced information, as well as using knowledge base 410 for the region and including information derived from the cohort features 404 such as crop type, the area under agriculture for each crop type, weather information, underlying farming activity, fertilizer data, calendar event data for the area, etc. Based at least in part on processing of the features extracted by cohorts analytics component 412, similar farms can be identified and clustered to form a cohort. Data from green points in a given cohort are processed using process-based model 414 (e.g., a DNDC model) to determine a farm-level time series of GHG emission estimates for each of the identified cohorts. The process-based model output can be validated using sensor data and/or by processing estimated farming practice data as activity data and using appropriate emission factors from one or more databases.

As also depicted in FIG. 4, one or more embodiments include steps for cohort classification and GHG emission estimation. Based on the extracted cohort features 404, a cohort classifier 416 (e.g., a classification model) is used to estimate a similarity score for any new farm pixel at non-GHG spatial resolution within the set of identified cohorts (detailed above). Also, time series GHG emission estimates 418 for the new farm pixel(s) can be generated based on the cohort's GHG estimate knowledge base 410 (computed as detailed above) and the similarity score(s) (generated by the cohort classifier 416) as a weighing factor.

As also illustrated in FIG. 4, one or more embodiments include a step for determining background GHG emission estimations. Static, physical and/or weather chemistry-based models are used by component 420 to estimate the background GHG emissions (e.g., daily background GHG emissions) from different sources such as water bodies, forests, power plants, traffic sources, residential sources, etc.

Additionally, FIG. 4 depicts steps for updating GHG emission estimates 428 using GHG bias correction learning model 422. In one or more embodiments, model 422 can include a time series learning model such as LSTM, etc., and such a model is used to learn the required bias correction for given GHG emission estimates at a non-GHG spatial resolution (i.e., finer than GHG satellite resolution) and a given temporal resolution (e.g., a daily temporal resolution), based at least in part on the time-series GHG estimates 418 (as detailed above), background GHG estimates via component 420 (as detailed above), and the nearest remote (coarse) GHG sensing data 424 from one or more remote sensing satellites with a distance measure as an input feature. GHG measurements from farm level sensors 426 are used to train and validate the bias correction learning model 422.

Figure 5:
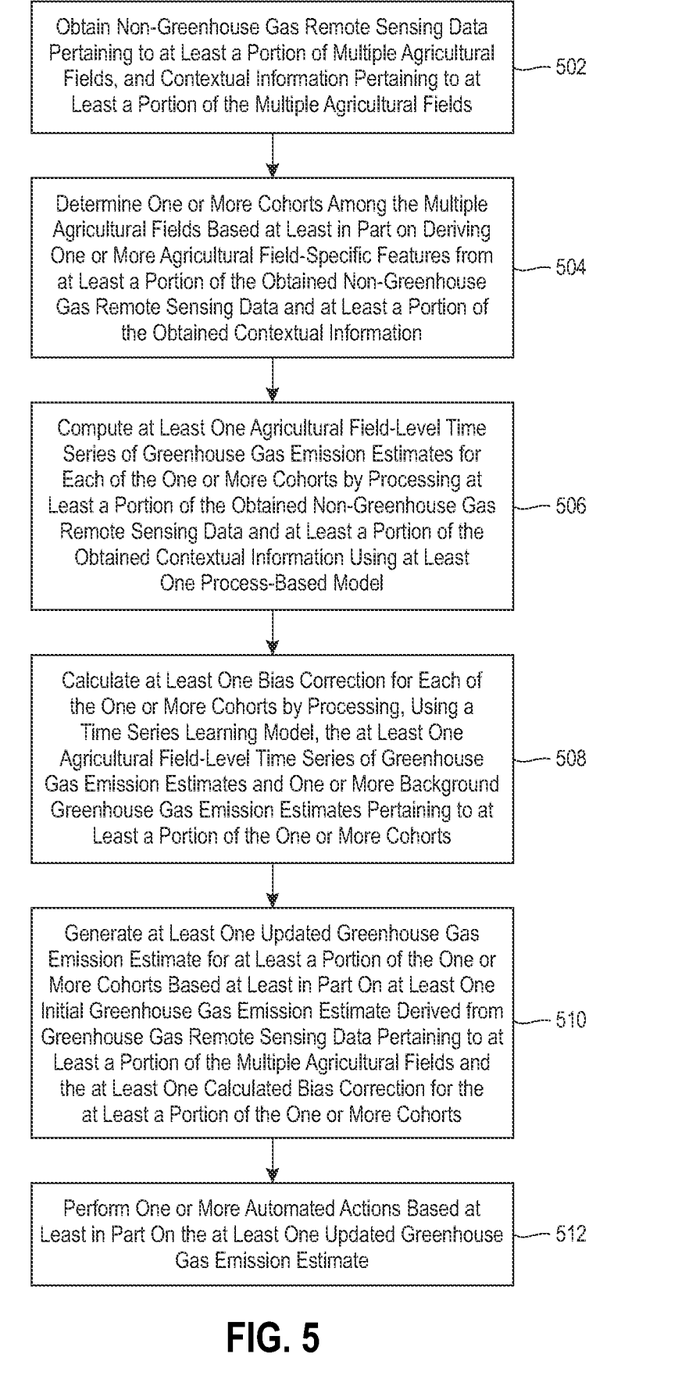
FIG. 5 is a flow diagram illustrating techniques according to an embodiment of the invention.

FIG. 5 is a flow diagram illustrating techniques according to an embodiment of the present invention. Step 502 includes obtaining non-greenhouse gas remote sensing data pertaining to at least a portion of multiple agricultural fields, and contextual information pertaining to at least a portion of the multiple agricultural fields. In one or more embodiments, obtaining non-greenhouse gas remote sensing data includes identifying usable non-greenhouse gas remote sensing data and non-usable data non-greenhouse gas remote sensing data based at least in part to one or more satellite limitations. Additionally or alternatively, obtaining non-greenhouse gas remote sensing data can include obtaining at least one of optical sensing data and microwave data, and obtaining contextual information can include obtaining one or more of calendar event data pertaining to at least a portion of the multiple agricultural fields, traffic information pertaining to at least a portion of the multiple agricultural fields, residential power consumption pertaining to at least a portion of the multiple agricultural fields, night light remote sensing data pertaining to at least a portion of the multiple agricultural fields, farming practices pertaining to at least a portion of the multiple agricultural fields, weather data pertaining to at least a portion of the multiple agricultural fields, and soil condition data pertaining to at least a portion of the multiple agricultural fields.

Step 504 includes determining one or more cohorts among the multiple agricultural fields based at least in part on deriving one or more agricultural field-specific features from at least a portion of the obtained non-greenhouse gas remote sensing data and at least a portion of the obtained contextual information. In at least one embodiment, determining one or more cohorts includes generating similarity scores, at non-greenhouse gas data spatial resolution, for at least a portion of the multiple agricultural fields by processing data pertaining to the one or more agricultural field-specific features using a classification model. Additionally or alternatively, deriving one or more agricultural field-specific features can include deriving at least one of one or more vegetation types associated with one or more of the multiple agricultural fields, one or more farming practices associated with one or more of the multiple agricultural fields, one or more crop cycles associated with one or more of the multiple agricultural fields, and crop acreage associated with one or more of the multiple agricultural fields.

Step 506 includes computing at least one agricultural field-level time series of greenhouse gas emission estimates for each of the one or more cohorts by processing at least a portion of the obtained non-greenhouse gas remote sensing data and at least a portion of the obtained contextual information using at least one process-based model. In one or more embodiments, computing at least one agricultural field-level time series of greenhouse gas emission estimates includes using at least a portion of the similarity scores as a weighing factor. Additionally or alternatively, processing at least a portion of the obtained non-greenhouse gas remote sensing data and at least a portion of the obtained contextual information using at least one process-based model can include processing at least a portion of the obtained non-greenhouse gas remote sensing data and at least a portion of the obtained contextual information using at least one denitrification-decomposition model. Further, one or more embodiments can include validating the at least one computed agricultural field-level time series one or more of using sensor data, estimated farming practice data associated with each of the one or more cohorts, and at least one emission factor derived from one or more databases.

Step 508 includes calculating at least one bias correction for each of the one or more cohorts by processing, using a time series learning model, the at least one agricultural field-level time series of greenhouse gas emission estimates and one or more background greenhouse gas emission estimates pertaining to at least a portion of the one or more cohorts. In at least one embodiment, calculating at least one bias correction for each of the one or more cohorts using a time series learning model includes calculating at least one bias correction for each of the one or more cohorts using a long short-term memory model.

Step 510 includes generating at least one updated greenhouse gas emission estimate for at least a portion of the one or more cohorts based at least in part on at least one initial greenhouse gas emission estimate derived from greenhouse gas remote sensing data pertaining to at least a portion of the multiple agricultural fields and the at least one calculated bias correction for the at least a portion of the one or more cohorts, wherein the at least one updated greenhouse gas emission estimate includes enhanced spatial resolution and temporal resolution as compared to the at least one initial greenhouse gas emission estimate.

Step 512 includes performing one or more automated actions based at least in part on the at least one updated greenhouse gas emission estimate. In at least one embodiment, performing one or more automated actions includes automatically training the time series learning model using the at least one updated greenhouse gas emission estimate.

Also, in one or more embodiments, software implementing the techniques depicted in FIG. 5 can be provided as a service in a cloud environment.

It is to be appreciated that "model," as used herein, refers to an electronic digitally stored set of executable instructions and data values, associated with one another, which are capable of receiving and responding to a programmatic or other digital call, invocation, or request for resolution based upon specified input values, to yield one or more output values that can serve as the basis of computer-implemented recommendations, output data displays, machine control, etc. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer.

The techniques depicted in FIG. 5 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an embodiment of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 5 can be implemented via a computer program product that can include computer useable program code that is stored in a computer readable storage medium in a data processing system, and wherein the computer useable program code was downloaded over a network from a remote data processing system. Also, in an embodiment of the invention, the computer program product can include computer useable program code that is stored in a computer readable storage medium in a server data processing system, and wherein the computer useable program code is downloaded over a network to a remote data processing system for use in a computer readable storage medium with the remote system.

An embodiment of the invention or elements thereof can be implemented in the form of an apparatus including a memory and at least one processor that is coupled to the memory and configured to perform exemplary method steps.

Figure 6:
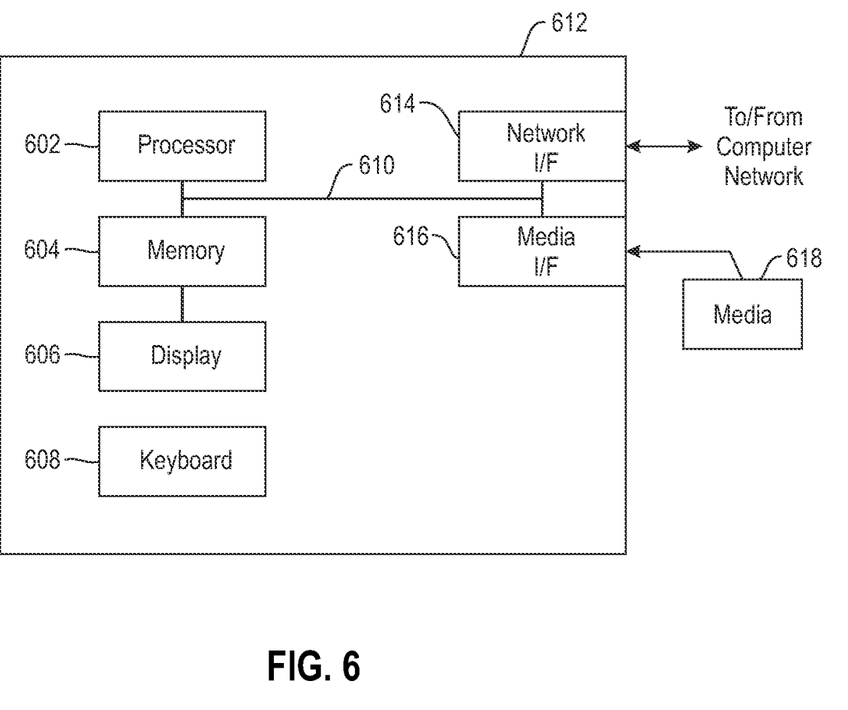
FIG. 6 is a system diagram of an exemplary computer system on which at least one embodiment of the invention can be implemented.

Additionally, an embodiment of the present invention can make use of software running on a computer or workstation. With reference to FIG. 6, such an implementation might employ, for example, a processor 602, a memory 604, and an input/output interface formed, for example, by a display 606 and a keyboard 608. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 602, memory 604, and input/output interface such as display 606 and keyboard 608 can be interconnected, for example, via bus 610 as part of a data processing unit 612. Suitable interconnections, for example via bus 610, can also be provided to a network interface 614, such as a network card, which can be provided to interface with a computer network, and to a media interface 616, such as a diskette or CD-ROM drive, which can be provided to interface with media 618.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 602 coupled directly or indirectly to memory elements 604 through a system bus 610. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including, but not limited to, keyboards 608, displays 606, pointing devices, and the like) can be coupled to the system either directly (such as via bus 610) or through intervening I/O controllers (omitted for clarity).

Network adapters such as network interface 614 may also be coupled to the system to enable the data processing system to become coupled to other data processing systems or remote printers or storage devices through intervening private or public networks. Modems, cable modems and Ethernet cards are just a few of the currently available types of network adapters.

As used herein, including the claims, a "server" includes a physical data processing system (for example, system 612 as shown in FIG. 6) running a server program. It will be understood that such a physical server may or may not include a display and keyboard.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 602. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed digital computer with associated memory, and the like. Given the teachings of the invention provided herein, one of ordinary skill in the related art will be able to contemplate other implementations of the components of the invention.

Additionally, it is understood in advance that implementation of the teachings recited herein are not limited to a particular computing environment. Rather, embodiments of the present invention are capable of being implemented in conjunction with any type of computing environment now known or later developed.

For example, cloud computing is a model of service delivery for enabling convenient, on-demand network access to a shared pool of configurable computing resources (for example, networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (for example, country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (for example, storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (for example, web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (for example, host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (for example, mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (for example, cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
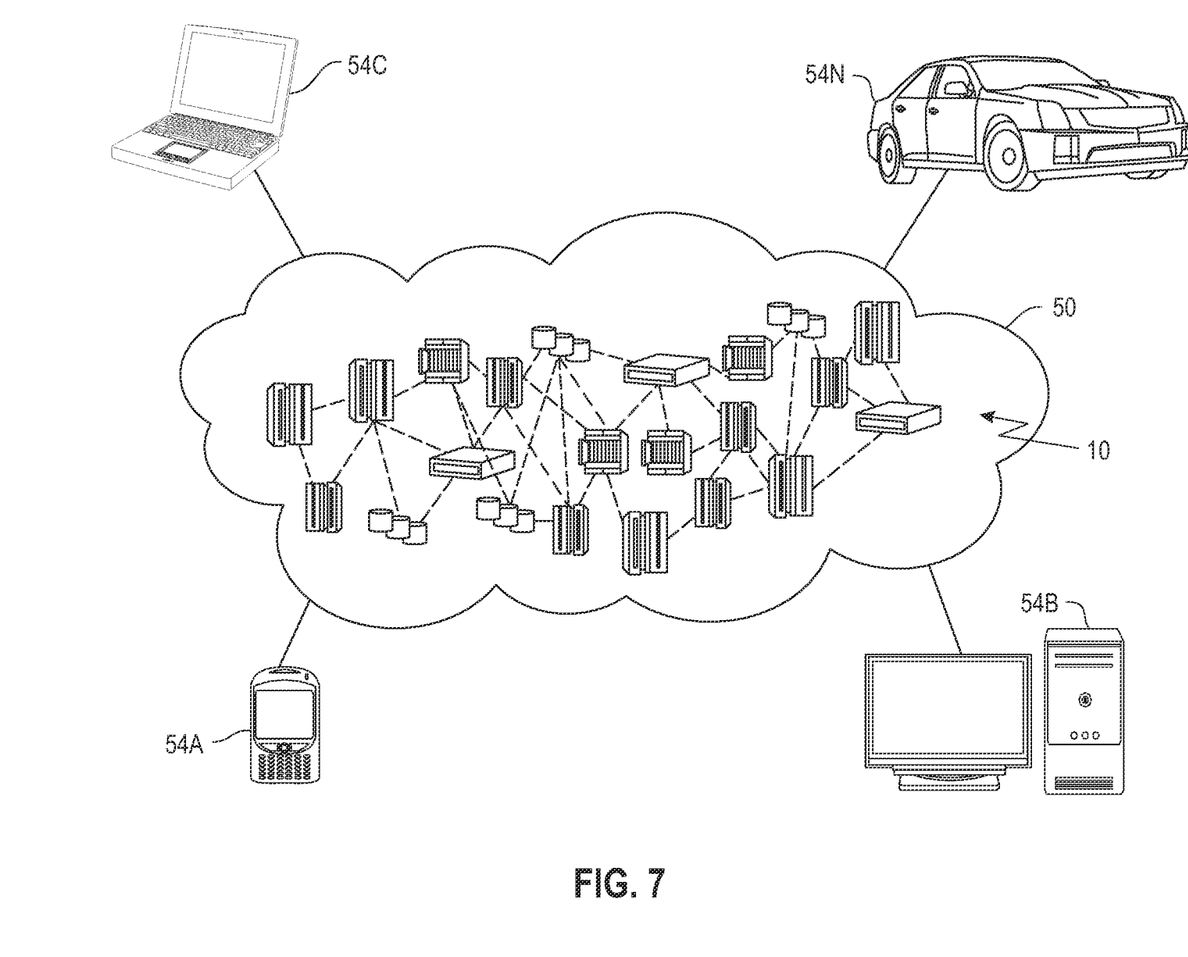
FIG. 7 depicts a cloud computing environment according to an embodiment of the present invention.

Referring now to FIG. 7, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 10 and cloud computing environment 50 can communicate with any type of computerized device over any type of network and/or network addressable connection (e.g., using a web browser).

Figure 8:
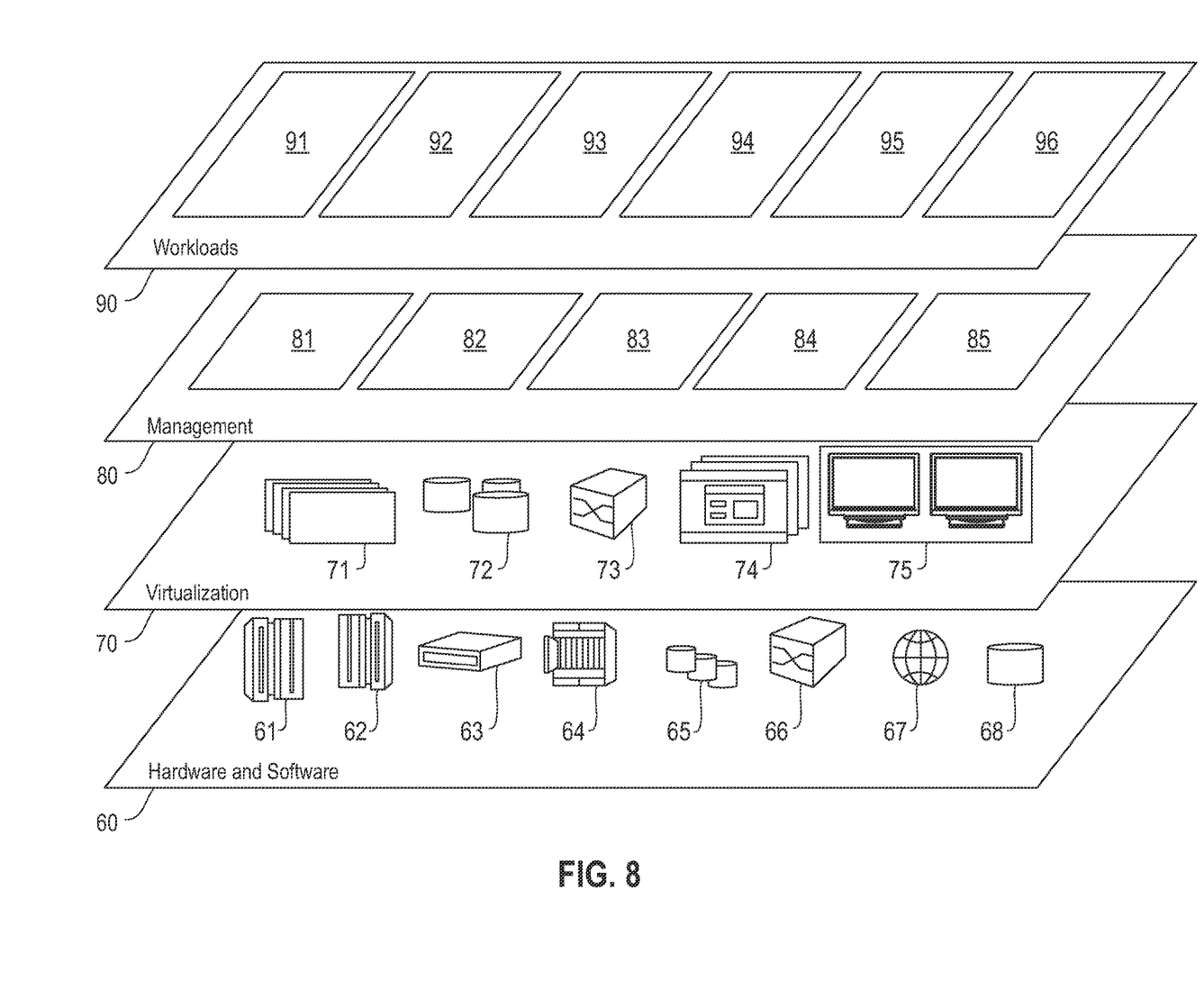
FIG. 8 depicts abstraction model layers according to an embodiment of the present invention.

Referring now to FIG. 8, a set of functional abstraction layers provided by cloud computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75. In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources.

In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and GHG emission estimate resolution enhancement 96, in accordance with the one or more embodiments of the present invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, enhancing spatial and temporal resolution of GHG emission estimates for agricultural fields.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   obtaining non-greenhouse gas remote sensing data pertaining to at least a portion of multiple agricultural fields, and contextual information pertaining to at least a portion of the multiple agricultural fields;
   determining one or more cohorts among the multiple agricultural fields based at least in part on deriving one or more agricultural field-specific features from at least a portion of the obtained non-greenhouse gas remote sensing data and at least a portion of the obtained contextual information;
   computing at least one agricultural field-level time series of greenhouse gas emission estimates for each of the one or more cohorts by processing at least a portion of the obtained non-greenhouse gas remote sensing data and at least a portion of the obtained contextual information using at least one process-based model;
   calculating at least one bias correction for each of the one or more cohorts by processing, using a time series learning model, the at least one agricultural field-level time series of greenhouse gas emission estimates and one or more background greenhouse gas emission estimates pertaining to at least a portion of the one or more cohorts;
   generating at least one updated greenhouse gas emission estimate for at least a portion of the one or more cohorts based at least in part on at least one initial greenhouse gas emission estimate derived from greenhouse gas remote sensing data pertaining to at least a portion of the multiple agricultural fields and the at least one calculated bias correction for the at least a portion of the one or more cohorts, wherein the at least one updated greenhouse gas emission estimate comprises enhanced spatial resolution and temporal resolution as compared to the at least one initial greenhouse gas emission estimate; and
   performing one or more automated actions based at least in part on the at least one updated greenhouse gas emission estimate, wherein performing one or more automated actions comprises automatically training at least a portion of the time series learning model using at least a portion of the at least one updated greenhouse gas emission estimate;
   wherein the method is carried out by at least one computing device.

2. The computer-implemented method of claim 1, wherein calculating at least one bias correction for each of the one or more cohorts using a time series learning model comprises calculating at least one bias correction for each of the one or more cohorts using a long short-term memory model.

3. The computer-implemented method of claim 1, wherein determining one or more cohorts comprises generating similarity scores, at non-greenhouse gas data spatial resolution, for at least a portion of the multiple agricultural fields by processing data pertaining to the one or more agricultural field-specific features using a classification model.

4. The computer-implemented method of claim 3, wherein computing at least one agricultural field-level time series of greenhouse gas emission estimates comprises using at least a portion of the similarity scores as a weighing factor.

5. The computer-implemented method of claim 1, wherein processing at least a portion of the obtained non-greenhouse gas remote sensing data and at least a portion of the obtained contextual information using at least one process-based model comprises processing at least a portion of the obtained non-greenhouse gas remote sensing data and at least a portion of the obtained contextual information using at least one denitrification-decomposition model.

6. The computer-implemented method of claim 1, further comprising:
   validating the at least one computed agricultural field-level time series one or more of using sensor data, estimated farming practice data associated with each of the one or more cohorts, and at least one emission factor derived from one or more databases.

7. The computer-implemented method of claim 1, wherein obtaining non-greenhouse gas remote sensing data comprises identifying usable non-greenhouse gas remote sensing data and non-usable data non-greenhouse gas remote sensing data based at least in part to one or more satellite limitations.

8. The computer-implemented method of claim 1, wherein obtaining non-greenhouse gas remote sensing data comprises obtaining at least one of optical sensing data and microwave data.

9. The computer-implemented method of claim 1, wherein obtaining contextual information comprises obtaining one or more of calendar event data pertaining to at least a portion of the multiple agricultural fields, traffic information pertaining to at least a portion of the multiple agricultural fields, residential power consumption pertaining to at least a portion of the multiple agricultural fields, night light remote sensing data pertaining to at least a portion of the multiple agricultural fields, farming practices pertaining to at least a portion of the multiple agricultural fields, weather data pertaining to at least a portion of the multiple agricultural fields, and soil condition data pertaining to at least a portion of the multiple agricultural fields.

10. The computer-implemented method of claim 1, wherein deriving one or more agricultural field-specific features comprises deriving at least one of one or more vegetation types associated with one or more of the multiple agricultural fields, one or more farming practices associated with one or more of the multiple agricultural fields, one or more crop cycles associated with one or more of the multiple agricultural fields, and crop acreage associated with one or more of the multiple agricultural fields.

11. The computer-implemented method of claim 1, wherein software implementing the method is provided as a service in a cloud environment.

12. A computer program product comprising a non-transitory computer readable storage medium having program instructions embodied therewith, the program instructions executable by a computing device to cause the computing device to:
- obtain non-greenhouse gas remote sensing data pertaining to at least a portion of multiple agricultural fields, and contextual information pertaining to at least a portion of the multiple agricultural fields;
- determine one or more cohorts among the multiple agricultural fields based at least in part on deriving one or more agricultural field-specific features from at least a portion of the obtained non-greenhouse gas remote sensing data and at least a portion of the obtained contextual information;
- compute at least one agricultural field-level time series of greenhouse gas emission estimates for each of the one or more cohorts by processing at least a portion of the obtained non-greenhouse gas remote sensing data and at least a portion of the obtained contextual information using at least one process-based model;
- calculate at least one bias correction for each of the one or more cohorts by processing, using a time series learning model, the at least one agricultural field-level time series of greenhouse gas emission estimates and one or more background greenhouse gas emission estimates pertaining to at least a portion of the one or more cohorts;
- generate at least one updated greenhouse gas emission estimate for at least a portion of the one or more cohorts based at least in part on at least one initial greenhouse gas emission estimate derived from greenhouse gas remote sensing data pertaining to at least a portion of the multiple agricultural fields and the at least one calculated bias correction for the at least a portion of the one or more cohorts, wherein the at least one updated greenhouse gas emission estimate comprises enhanced spatial resolution and temporal resolution as compared to the at least one initial greenhouse gas emission estimate; and
- perform one or more automated actions based at least in part on the at least one updated greenhouse gas emission estimate, wherein performing one or more automated actions comprises automatically training at least a portion of the time series learning model using at least a portion of the at least one updated greenhouse gas emission estimate.

13. The computer program product of claim 12, wherein calculating at least one bias correction for each of the one or more cohorts using a time series learning model comprises calculating at least one bias correction for each of the one or more cohorts using a long short-term memory model.

14. The computer program product of claim 12, wherein determining one or more cohorts comprises generating similarity scores, at non-greenhouse gas data spatial resolution, for at least a portion of the multiple agricultural fields by processing data pertaining to the one or more agricultural field-specific features using a classification model.

15. The computer program product of claim 14, wherein computing at least one agricultural field-level time series of greenhouse gas emission estimates comprises using at least a portion of the similarity scores as a weighing factor.

16. The computer program product of claim 12, wherein processing at least a portion of the obtained non-greenhouse gas remote sensing data and at least a portion of the obtained contextual information using at least one process-based model comprises processing at least a portion of the obtained non-greenhouse gas remote sensing data and at least a portion of the obtained contextual information using at least one denitrification-decomposition model.

17. The computer program product of claim 12, wherein obtaining non-greenhouse gas remote sensing data comprises identifying usable non-greenhouse gas remote sensing data and non-usable data non-greenhouse gas remote sensing data based at least in part to one or more satellite limitations.

18. A system comprising:
- a memory configured to store program instructions; and
- a processor operatively coupled to the memory to execute the program instructions to:
  - obtain non-greenhouse gas remote sensing data pertaining to at least a portion of multiple agricultural fields, and contextual information pertaining to at least a portion of the multiple agricultural fields;
  - determine one or more cohorts among the multiple agricultural fields based at least in part on deriving one or more agricultural field-specific features from at least a portion of the obtained non-greenhouse gas remote sensing data and at least a portion of the obtained contextual information;
  - compute at least one agricultural field-level time series of greenhouse gas emission estimates for each of the one or more cohorts by processing at least a portion of the obtained non-greenhouse gas remote sensing data and at least a portion of the obtained contextual information using at least one process-based model;
  - calculate at least one bias correction for each of the one or more cohorts by processing, using a time series learning model, the at least one agricultural field-level time series of greenhouse gas emission estimates and one or more background greenhouse gas emission estimates pertaining to at least a portion of the one or more cohorts;
  - generate at least one updated greenhouse gas emission estimate for at least a portion of the one or more cohorts based at least in part on at least one initial greenhouse gas emission estimate derived from greenhouse gas remote sensing data pertaining to at least a portion of the multiple agricultural fields and the at least one calculated bias correction for the at least a portion of the one or more cohorts, wherein the at least one updated greenhouse gas emission estimate comprises enhanced spatial resolution and temporal resolution as compared to the at least one initial greenhouse gas emission estimate; and
  - perform one or more automated actions based at least in part on the at least one updated greenhouse gas emission estimate, wherein performing one or more automated actions comprises automatically training at least a portion of the time series learning model using at least a portion of the at least one updated greenhouse gas emission estimate.

19. The system of claim 18, wherein calculating at least one bias correction for each of the one or more cohorts using a time series learning model comprises calculating at least one bias correction for each of the one or more cohorts using a long short-term memory model.

20. The system of claim 18, wherein determining one or more cohorts comprises generating similarity scores, at non-greenhouse gas data spatial resolution, for at least a portion of the multiple agricultural fields by processing data pertaining to the one or more agricultural field-specific features using a classification model.

* * * * *